United States Patent [19]

Grüner et al.

[11] Patent Number: 5,097,938
[45] Date of Patent: Mar. 24, 1992

[54] APPARATUS FOR TRANSFERRING TEST STRIPS TO AN EXAMINING APPARATUS

[75] Inventors: Hans-Peter Grüner, Mannheim; Jürgen Schildhorn, Altrip; Stephan Sattler, Söcking, all of Fed. Rep. of Germany

[73] Assignee: Boehringer Mannheim GmbH, Mannheim-Waldhof, Fed. Rep. of Germany

[21] Appl. No.: 320,548

[22] Filed: Mar. 8, 1989

[30] Foreign Application Priority Data

Mar. 8, 1988 [DE] Fed. Rep. of Germany ....... 3807565

[51] Int. Cl.$^5$ .............................................. B65G 47/24
[52] U.S. Cl. ...................................... 198/397; 198/399
[58] Field of Search ............... 198/397, 399, 400, 444, 198/453, 608, 463.5, 524; 118/686, 687, 322

[56] References Cited

U.S. PATENT DOCUMENTS

| | | | |
|---|---|---|---|
| 2,662,633 | 12/1953 | Kingsley | 198/444 X |
| 3,115,235 | 12/1963 | Othon | 198/399 X |
| 3,526,311 | 9/1970 | Robinson | 198/400 |
| 3,537,567 | 11/1970 | Nowicki | 198/399 |
| 4,306,647 | 12/1981 | Boucherie | 198/399 X |
| 4,479,573 | 10/1984 | Ackley, Sr. et al. | 198/397 X |
| 4,721,230 | 1/1988 | McKnight | 198/400 X |
| 4,721,298 | 1/1988 | Pitcher | 271/303 |
| 4,777,907 | 10/1988 | Sänger | 118/687 |
| 4,796,744 | 1/1989 | Sänger | 198/397 |
| 4,867,298 | 9/1989 | Milliner et al. | 198/524 X |

FOREIGN PATENT DOCUMENTS

| | | |
|---|---|---|
| 0071856 | 2/1983 | European Pat. Off. ......... 198/463.5 |
| 0180792 | 5/1986 | European Pat. Off. . |
| 0255070 | 2/1988 | European Pat. Off. . |
| 0255077 | 2/1988 | European Pat. Off. . |
| 0255675 | 2/1988 | European Pat. Off. . |
| 0211213 | 9/1986 | Japan ................................ 198/397 |

*Primary Examiner*—Robert P. Olszewski
*Assistant Examiner*—James R. Bidwell
*Attorney, Agent, or Firm*—Foley & Lardner

[57] ABSTRACT

Apparatus for transferring test strips (T), which have detectably different sides and ends, to an examining apparatus, having a collecting chamber for receiving a loose bundle of test strips (T) in which identical ends point in the same direction, having a separator which feeds the test strips (T) individually to a slide member which is movable back and forth between a receiving station and a delivery station, and having a turner controlled by a detector, the turner ensuring that all the test strips (T) in the delivery station are arranged on the slide member with identical sides facing upwards, characterized in that the separator has a chute terminating over the receiving station, from which the test strips (T) are individually fed, with a longitudinal edge pointing downwards, to a deflector controlled by the detector, the deflector sending the test strips (T) away with identical sides facing upwards.

12 Claims, 6 Drawing Sheets

APPARATUS FOR TRANSFERRING TEST STRIPS TO AN EXAMINING APPARATUS

The invention relates to an apparatus for transferring test strips. In one embodiment, this invention relates to an apparatus for transferring test strips (T), which have detectably different sides and ends, to an examining apparatus, having a collecting chamber (4) for receiving a loose bundle of test strips (T) in which identical ends point in the same direction, having a separator (6) which feeds the test strips (T) individually to a slide member (8) which is movable back and forth between a receiving station and a delivery station, and having a turner (12) controlled by a detector (10), said turner (12) ensuring that all the test strips (T) in the delivery station are arranged on the slide member (8) with identical sides facing upwards.

In an apparatus of this kind known from the European Patent Application published under the No. 0180792, the base of the collecting chamber is formed essentially by the surface of the slide member. The slide member has transverse grooves for receiving the test strips. The turning means are at the end of the stroke of the slide member behind the delivery station of the slide member. Any test strips which are not correctly located in the transverse grooves of the slide member are pulled out of the transverse grooves by the turning means and turned around.

This apparatus operates only with test strips which exactly fit the transverse grooves, which are not substantially bent and which are strong enough to withstand the turning means which mechanically handles them. In addition, the controlling of the slide member is a very laborious process.

The aim of the invention is to provide an apparatus for transferring test strips (T), which have detectably different sides and ends, to an examining apparatus, having a collecting chamber (4) for receiving a loose bundle of test strips (T) in which identical ends point in the same direction, having a separator (6) which feeds the test strips (T) individually to a slide member (8) which is movable back and forth between a receiving station and a delivery station, and having a turner (12) controlled by a detector (10), said turner (12) ensuring that all the test strips (T) in the delivery station are arranged on the slide member (8) with identical sides facing upwards which apparatus is capable of separating test strips of different shapes and feeding them to the delivery station in the correct position and which is able to handle even bent test strips and those of limited stability, whilst being relatively easy to control.

The solution to this aim is provided by an apparatus for transferring test strips (T), which have detectably different sides and ends, to an examining apparatus, having a collecting chamber (4) for receiving a loose bundle of test strips (T) in which identical ends point in the same direction, having a separator (6) which feeds the test strips (T) individually to a slide member (8) which is movable back and forth between a receiving station and a delivery station, and having a turner (12) controlled by a detector (10), said turner (12) ensuring that all the test strips (T) in the delivery station are arranged on the slide member (8) with identical sides facing upwards, characterized in that the separator (6) has a chute (14) terminating over the receiving station, from which the test strips (T) are individually fed, with a longitudinal edge pointing downwards, to a trapezoid shaped deflector having concave sides (16) controlled by the detector (10), said deflector (16) sending the test strips (T) away with identical sides facing upwards.

The chute and the deflector make it possible to supply test strips of different widths, possibly bent and not particularly strong to the slide member. No transverse grooves are needed on the surface of the slide member. The deflector is comparatively easy to control.

A particularly simple form of deflector is formed by a deflector body (16) pivotably mounted under the mouth of the chute (14) and having the cross sectional form of a trapezium with concave sides.

To ensure that only one test strip is supplied to the deflector at any one time, the construction provides at least one blocking member (18, 24, 26) in the lower part of the chute (14) for the test strips (T) which is to be inserted in the chute (14); A constructionally favourable position of the detector is at the lower end of the chute (14).

A particularly reliable method of separation of the test strips before they are inserted in the chute is where the collecting chamber (4) has two base portions (32, 34) which converge downwardly in a V-shape, the first (32) of which is attached to the apparatus whilst the second (34) is capable of being raised periodically to allow the test strips (T) through and the base portion (32) attached to the apparatus is extended as far as the circumference of a rotating first roller (44) which comprises grooves (46) for receiving individual test strips (T) (extension 42); and where adjacent the first roller (44) is a first plate (48) directed diagonally downwards, which receives test strips (T) released from the grooves (46) of the first roller (44) and feeds them to a rotating second roller (52) which comprises grooves (50) for receiving individual test strips (T); and adjoining the second roller (52), is a second plate (68) directed diagonally downwards, which receives test strips (T) released from the grooves (50) of the second roller (52) and feeds them to a rotating third roller (72) which comprises grooves (70) for receiving individual test strips (T). The third roller (0.72) may optionally be the only roller and may also if desired be located immediately after the first roller.

Reliable insertion of the test strips into the grooves of the first and/or second roller is achieved if these grooves are constructed in that the grooves (46, 50) of the first and second rollers (44, 52) have boundary surfaces (76, 78) extending at an acute angle to each other, the upstream surface (76), as it receives a test strip (T), extending substantially parallel to the surface of the releasing plate (42, 48) whilst the downstream surface (78), as it releases a test strip (T), extends substantially parallel to the surface of the receiving plate (46, 68).

The grooves in the third roller are preferably constructed in that the grooves (70) of the third roller (72) have a right-angled cross-section which is somewhat deeper than the thickness of the test strips (T), in order to achieve particularly reliable separation which will be explained in the specific description which follows.

A particularly simple method of control of the first roller, the second roller and the periodic raising of the second base portion of the collecting chamber characterized in that, nearest the lower end of the second plate (68), there is a detector (80) which is responsive to the test strips (T), said detector (80) controlling the rotation of the first roller (44), the second roller (52) and the periodic lifting of the second base portion (34) of the collecting chamber (4).

To prevent extremely bent test strips from entering the collecting chamber, an arrangement wherein adjacent the third roller (72) there is preferably provided a paring blade (82) for taking out and removing any test strips (T) projecting beyond the grooves (70) of the third roller (72).

In order to enable the test strips to be moistened at the delivery station of the slide member, an arrangement is preferably provided wherein above the delivery station of the slide member (8) there is provided a device for moistening (direction of the arrow F) the test strips T, and below the delivery station of the slide member (8) there is provided a tank (94).

The invention is hereinafter described by means of embodiments by way of example, referring to the accompanying drawings.

FIG. 5 shows, on a larger scale, part of the third roller cooperating with the second roller.

Figure 1:
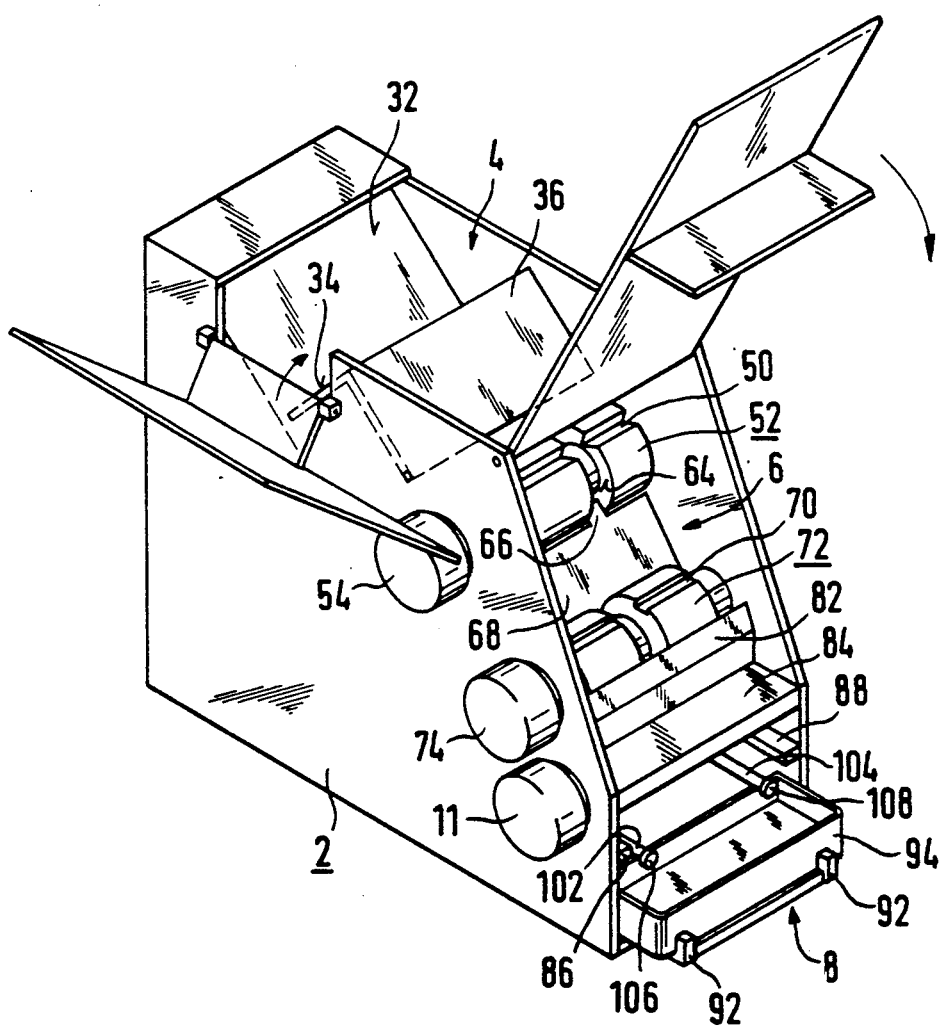
FIG. 1 shows a perspective view of the apparatus.
Figure 2:
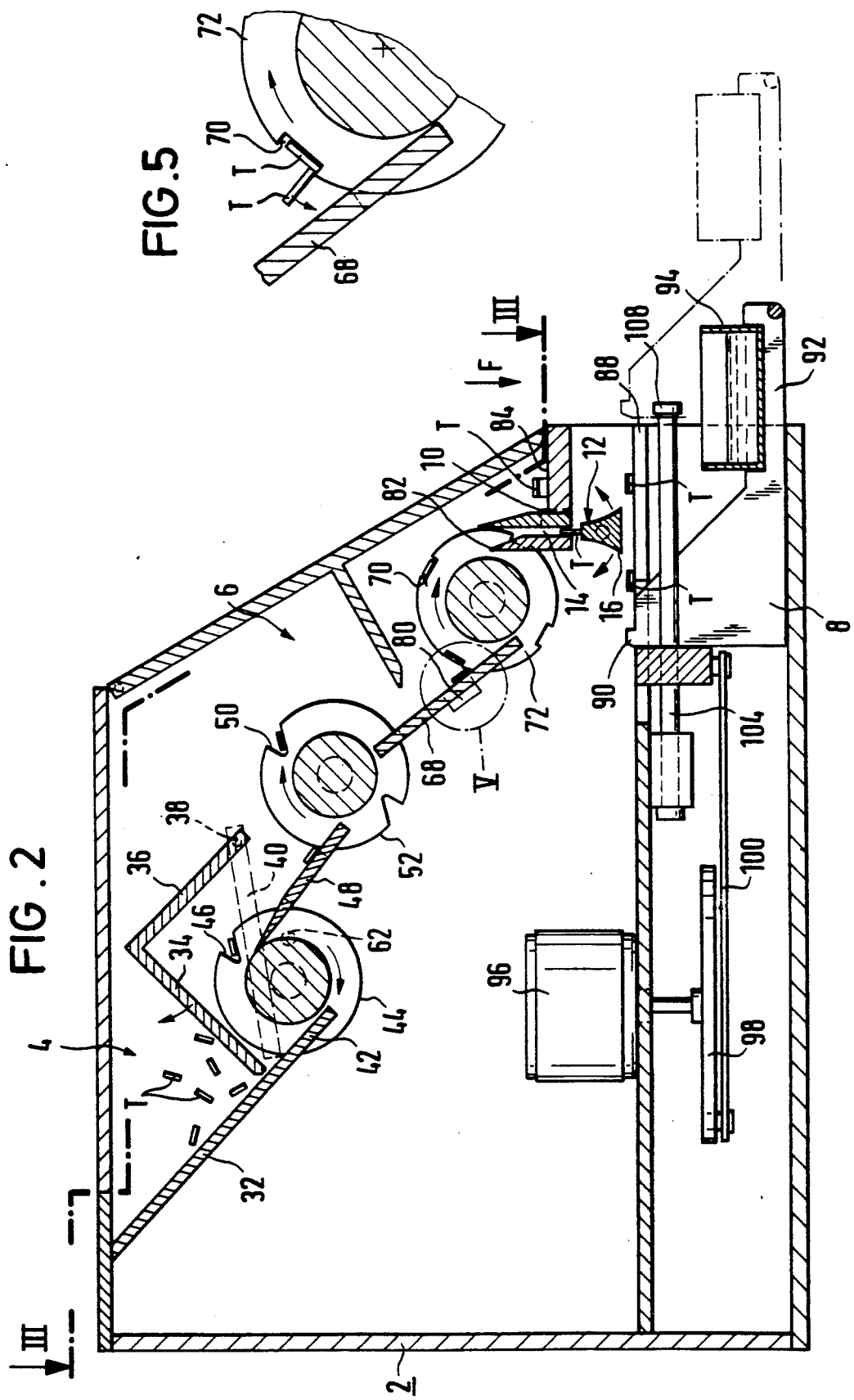
FIG. 2 shows a longitudinal section through the apparatus along the section line II—II of FIG. 3.
Figure 3:
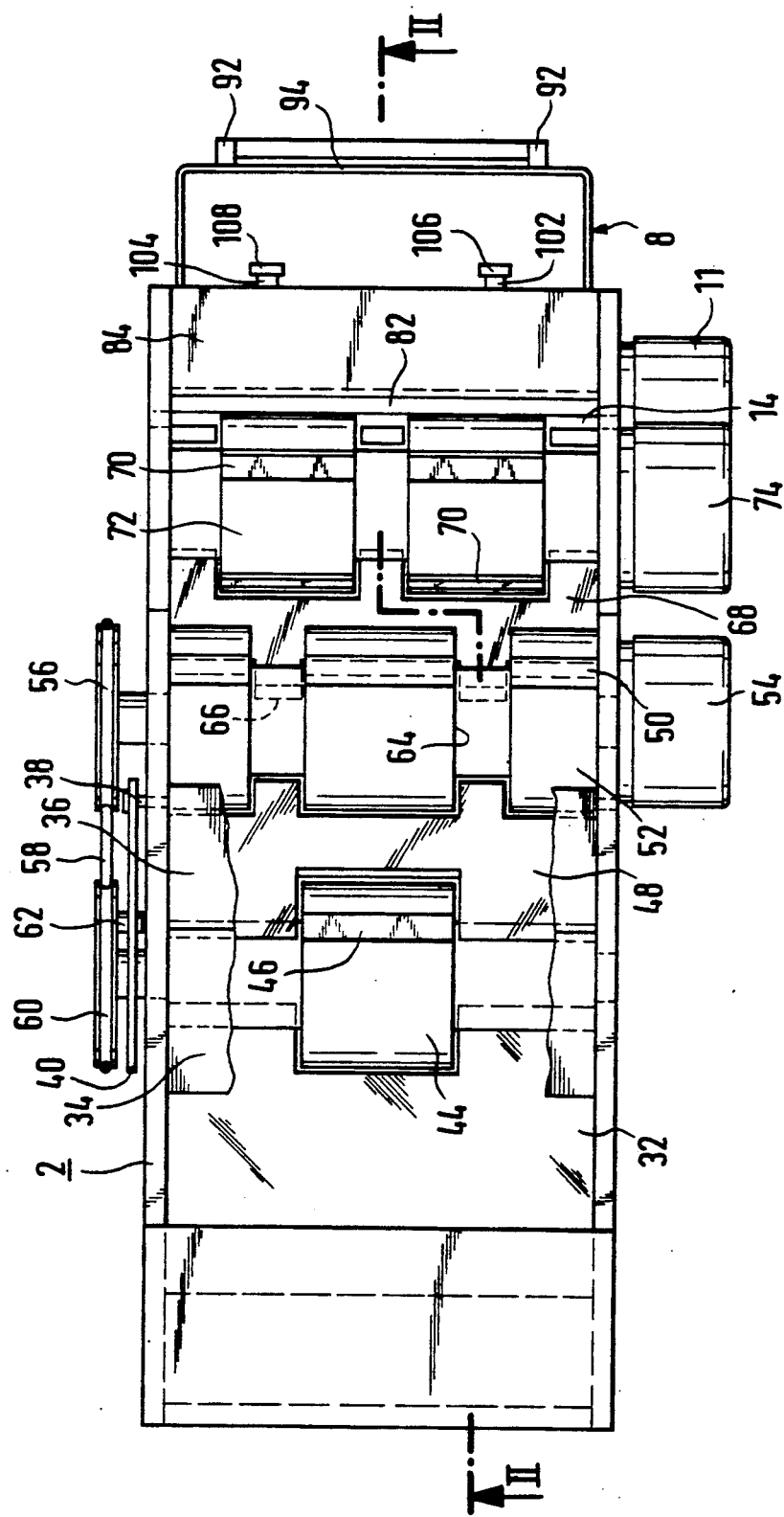
FIG. 3 shows a section through the apparatus along the section line III—III in FIG. 2.
Figure 4:
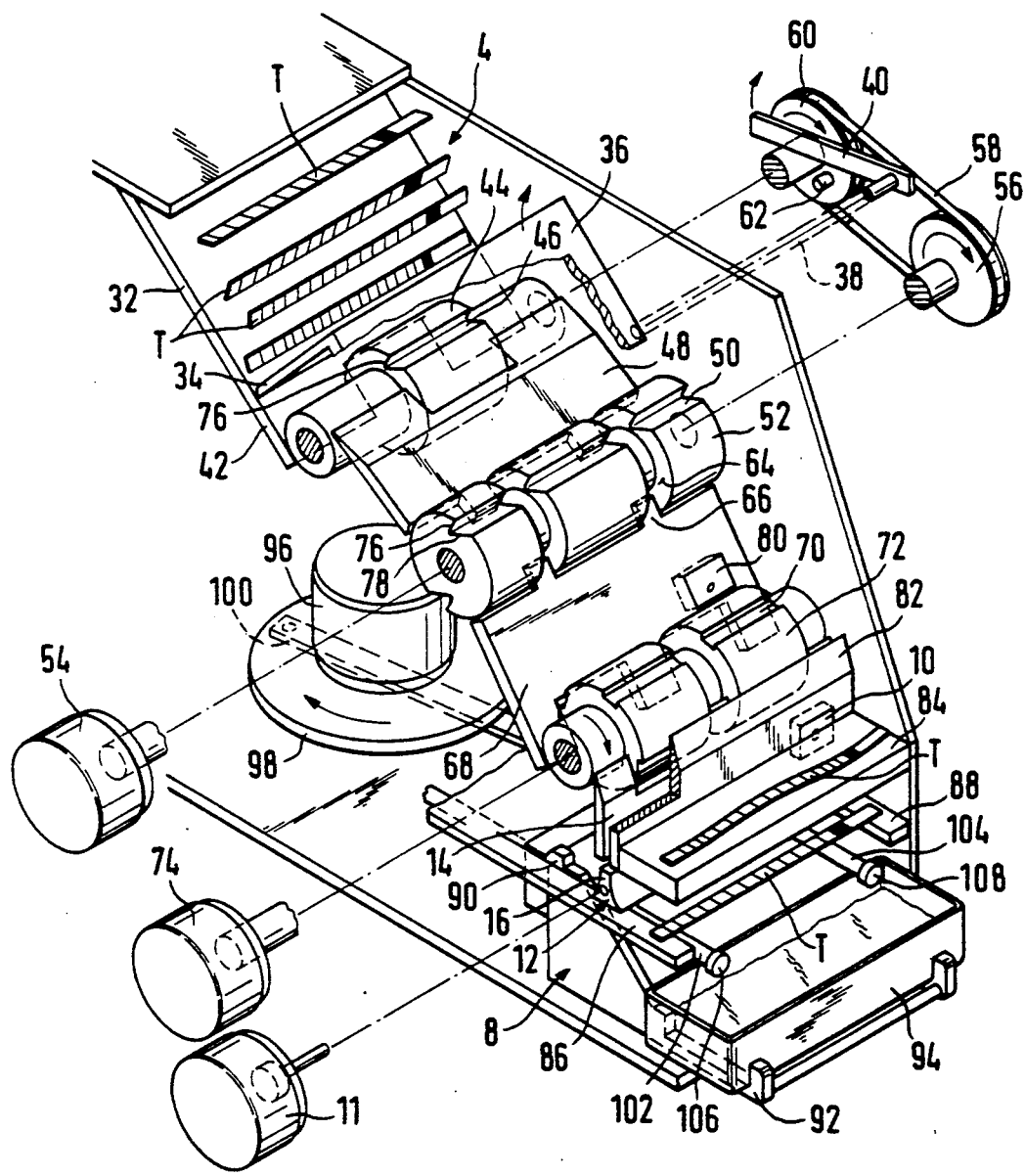
FIG. 4 shows, in perspective, the interaction of the individual elements of the apparatus.

The apparatus according to the embodiments by way of example has a housing 2 with a collecting chamber 4 for receiving a loose bundle of test strips T in which similar ends are pointing in the same direction. A separator 6 is provided which individually supplies the test strips T to a slide member 8 which is movable back and forth between a receiving station (FIG. 2, continuous lines) and a delivery station (FIG. 2, broken lines). A turner 12 controlled by a detector 10 ensures that all the test strips T in the delivery station are arranged on the slide member 8 with similar sides facing upwards.

The separator 6 has a chute 14 terminating above the receiving station, from which the test strips T are individually supplied, with a longitudinal edge pointing downwards, to a deflector 16 controlled by the detector 10, this detector 16 guiding the test strips T onto the slide member 8 with similar sides facing upwards. The tilting of the deflector 16 is carried out by means of a motor 11 controlled by the detector 10.

Figure 6:
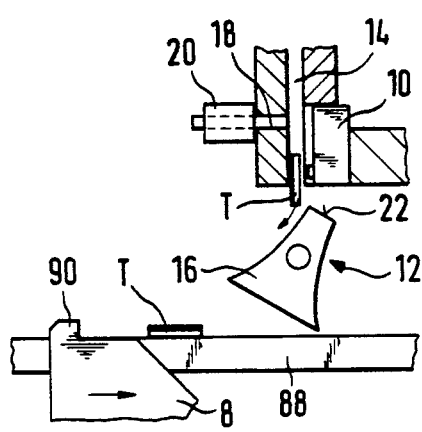
FIGS. 6, 7 and 8 show a first embodiment of the chute and deflector in different operational states.
Figure 7:
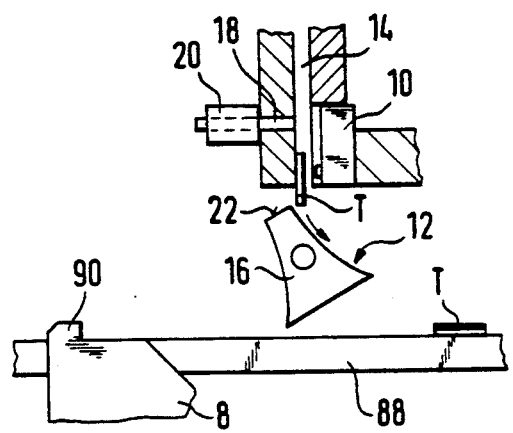
Figure 8:
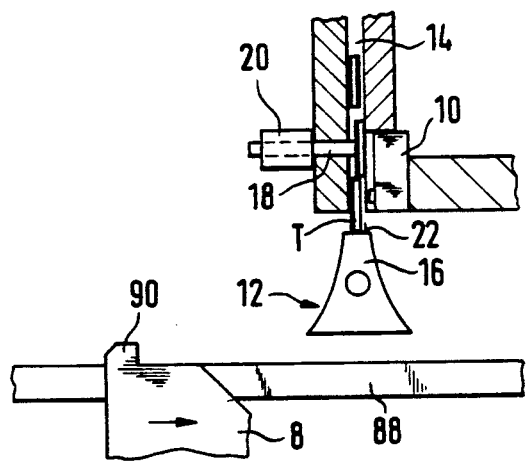

In the embodiment shown in FIGS. 6 to 8, in the lower part of the chute 14, opposite and above the detector 10, there is a blocking member 18 for the test strips T, which is to be inserted in the chute, this blocking member being capable of holding a test strip T and ensuring that only the preceding test strip T reaches the deflector body 16. The blocking member 18 is controlled by an electromagnet 20 mounted on the outside of the chute 14. The electromagnet 20 is controlled by the detector 10.

Figure 9:
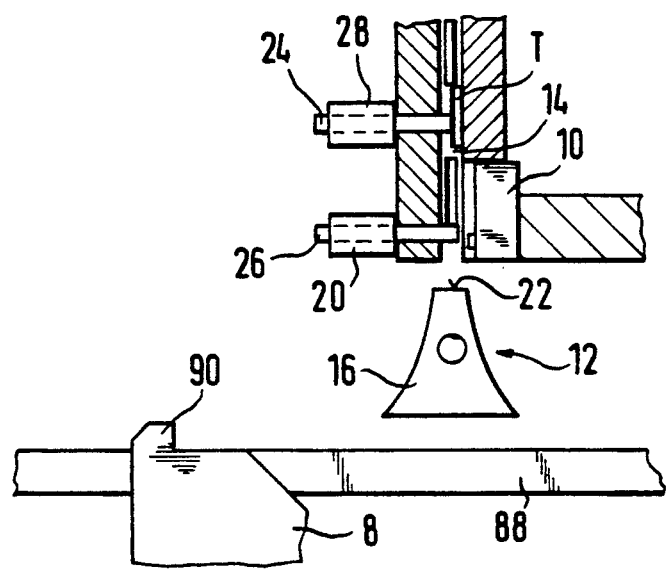
FIG. 9 shows a second embodiment of the chute and deflector.

Whereas in the embodiment according to FIGS. 6 to 8 the upper boundary surface 22 of the deflector body 16 acts as an abutment for the test strip T located in front of the detector 10, in the embodiment according to FIG. 9 there are two blocking members 24, 26 arranged one above the other with associated electromagnets 28, 20. These blocking members 24, 26 are controlled alternately by the detector 10 by means of the electromagnets 28, 20. The abutment for the lowest test strip T in this case is the lower blocking member 26.

Figure 10:
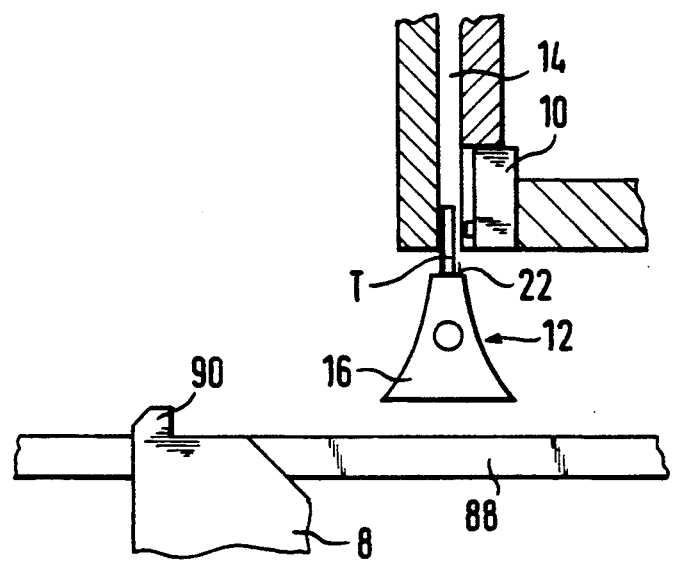
FIG. 10 shows a third embodiment of the chute and deflector.

In the embodiment according to FIG. 10, no blocking member at all is provided. Only one test strip T is able to enter the chute 14 and then abuts on the upper boundary surface 22 of the deflector body 16.

The collecting chamber 4 has two base portions 32, 34 converging downwardly in a V-shape. The base portion 32 is attached to the apparatus. The base portion 34 is angularly mounted on a carrier plate 36, from which proceeds a spindle 38 pivotably mounted in the housing 2. At the outer end of the shaft 38 is a lever arm 40 for pivoting the base portion 34 in order to release the test strips T located in the collecting chamber 4 through an opening which will then appear, leading to an extension 42 of the base portion 32 attached to the apparatus. At the other end of the extension 42 is a roller 44, mounted in the housing 2, having grooves 46 for receiving individual test strips T which slide down onto the extension 42.

Adjoining the first roller 44 is a plate 48 directed diagonally downwards and enclosing the end faces of this roller 44, said plate 48 receiving the test strips T released from the grooves 46 of the roller 44 and feeding them to a rotating second roller 52 which comprises grooves 50 for receiving individual test strips T. The roller 52 is driven by a first motor on the output shaft of which is located a belt pulley 56 for driving a belt 58 which drives a belt pulley 60 located on the spindle of the roller 44. The lever arm 40 is raised and lowered, in accordance with the rotation of the belt pulley 60, by a pin 62 provided on the belt pulley 60.

The second roller 52 has circumferential grooves 64 into which the attachments 66 of a second plate 68 project, said second plate 68 being directed diagonally downwards and adjoining the second roller 52. The second plate 68 receives the test strips T released from the grooves 50 in the second roller 52 and feeds them to a rotating third roller 72 comprising grooves 70 for receiving individual test strips T. The third roller 72 is driven by a motor 74. The grooves 46, 50 of the rollers 44, 52 have boundary surfaces 76, 78 extending at an acute angle to one another, the upstream boundary surface 76, as it receives a test strip T, extending substantially parallel to the surface of the releasing plate 42 or 48, whilst the downstream surface 78, as it delivers a test strip T, extends substantially parallel to the surface of the receiving plate 48 or 68. In the embodiment shown, the planes of the boundary surfaces 76, 78 are both located on one and the same side of the spindles of the associated rollers 44, 52, which has proved particularly favourable for the separation process.

The grooves 70 of the third roller 72 have a rightangled cross-section which is somewhat deeper than the thickness of the test strips T. If, by chance, two test strips T land one on top of the other in a groove 70, as shown in FIG. 5, the rotation of the roller 72 tips the upper test strip T back onto the plate 68 so that it slides into the next groove 70.

Next to the lower end of the second plate 68, there is provided a detector 80 which responds to the test strips T and controls the rotation of the first roller 44 and second roller 52 and the periodic lifting of the second base portion 34 of the collecting chamber 4 by controlling the motor 54.

Adjoining the third roller 72 is a paring blade 82 for taking out and removing any test strips T projecting beyond the grooves 70. The test strips T taken out drop onto a collecting area 84.

After leaving the chute 14 the test strips T arranged in the desired position initially rest on support arms 86, 88 which support the ends of the test strips T. The test strips T are transferred from the support arms 86, 88 by means of cams 90 on the slide member 8 to the delivery station, where they are wetted by liquid applied to them from above (direction of arrow F). The slide member or carriage 8 has, on forward pointing arms 92, a tank 94 for holding the liquid.

The back and forth movement of the slide member 8 is effected by means of a motor 96 which drives a connecting rod 100 acting on the slide member 8 via a crank disc 98.

The slide member 8 is guided by guide rods 102, 104 which have contact heads 106, 108 on their ends.

We claim:

1. An apparatus for transferring test strips having detectably different sides and ends to an examining apparatus comprising a collecting chamber for receiving a loose bundle of test strips in which identical ends point in the same direction, a conveyor which is movable between a receiving station and a delivery station, a separator comprising a chute terminating over said receiving station which feeds the test strips individually with a longitudinal edge pointing downwards to said conveyor, a detector for detecting the orientation of the sides of a test strip in said separator chute, and a deflector controlled by said detector for selectively turning test strips from said separator chute to ensure that all the test strips in the delivery station are received on the conveyor with identical sides facing upwards, wherein said deflector comprises a deflector body having the cross sectional configuration of a trapezoid with concave sides pivotably mounted under the mouth of said chute, which sides receive said test strips from said chute.

2. An apparatus as claimed in claim 1, further comprising at least one blocking member extendable into the lower part of said chute for blocking said test strips.

3. An apparatus as claimed in claim 1, wherein said detector is arranged at the lower end of said chute.

4. An apparatus as claimed in claim 1, wherein said collecting chamber comprises first and second base portions which converge downwardly in a V-shape, said first base portion being attached to the apparatus, and said second base portion being periodically raisable to permit test strips to exit said collecting chamber, said first base portion being extended to the circumference of a rotating first roller, and said first roller comprising grooves for receiving individual test strips.

5. An apparatus as claimed in claim 4, further comprising a diagonally downwardly directed first plate for receiving test strips from the grooves of said first roller and feeding them to a rotating second roller comprising grooves for receiving individual test strips.

6. An apparatus as claimed in claim 5, further comprising a diagonally downwardly directed second plate adjoining the second roller, for receiving test strips from the grooves of the second roller and feeding them to a rotating third roller comprising grooves for receiving individual test strips.

7. An apparatus as claimed in claim 6, wherein grooves of said first and second rollers have upstream and downstream boundary surfaces extending at an acute angle to each other, the upstream surface, as it receives a test strip, extending substantially parallel to the surface of the first plate, and the downstream surface, as it releases a test strip, extending substantially parallel to the surface of the second plate.

8. An apparatus as claimed in claim 6, wherein the grooves of said third roller have a rectangular crosssection which is slightly deeper than the thickness of the test strips.

9. An apparatus as claimed in claim 6, further comprising a detector responsive to said test strips adjacent the lower end of the second plate, for controlling the rotation of said first roller, said second roller, and the periodic lifting of said second base portion of said collecting chamber.

10. An apparatus as claimed in claim 6, further comprising a paring blade adjacent said third roller, for extracting and removing any test strips projecting beyond the grooves of said third roller.

11. An apparatus as claimed in claim 1, further comprising a moistening device above the delivery station of the slide member for moistening the test strips, and a tank below said delivery station.

12. An apparatus as claimed in claim 1, wherein the conveyor is a slide member which reciprocates between the receiving station and the delivery station.

* * * * *